United States Patent [19]

Bach et al.

[11] 4,346,239

[45] * Aug. 24, 1982

[54] PROCESS FOR THE PREPARATION OF 2-METHYLENE ALDEHYDES

[75] Inventors: Hanswilhelm Bach, Duisburg; Eike Brundin, Dinslaken; Wilhelm Gick, Duisburg-Baerl, all of Fed. Rep. of Germany

[73] Assignee: Ruhrchemie AG, Oberhausen, Fed. Rep. of Germany

[ * ] Notice: The portion of the term of this patent subsequent to Aug. 11, 1998, has been disclaimed.

[21] Appl. No.: 220,382

[22] Filed: Dec. 29, 1980

Related U.S. Application Data

[63] Continuation-in-part of Ser. No. 106,211, Dec. 21, 1979.

[30] Foreign Application Priority Data

Jul. 4, 1980 [DE] Fed. Rep. of Germany ....... 3025350

[51] Int. Cl.$^3$ .............................................. C07C 47/22
[52] U.S. Cl. ..................................... 568/461; 568/433; 568/459; 568/463; 568/464
[58] Field of Search ............... 568/464, 463, 459, 420, 568/461, 433

[56] References Cited

U.S. PATENT DOCUMENTS

| | | | |
|---|---|---|---|
| 2,518,416 | 8/1950 | Bortinick | 568/459 |
| 2,639,295 | 5/1953 | Hagemeyer | 568/459 |
| 3,463,818 | 8/1969 | Blumenthal | 568/459 |
| 4,283,564 | 8/1981 | Berhagen et al. | 568/461 |

FOREIGN PATENT DOCUMENTS 1957301  5/1971  Fed. Rep. of Germany ...... 568/464

OTHER PUBLICATIONS

Smith "Acrolein" Wiley & Sons, N.Y. '1962 pp. 211–244, 8.4–8.5.
Takashi "Chemical Abstracts" vol. 60, p. 2775
Farberov et al. "Chemical Abstracts" vol. 59, pp. 393–394 (1963).
Malinowshi et al. "Chemical Abstracts" vol. 56, pp. 2321–2322 (1962).
"Handbook of Chemistry & Physics" 55th ed. (1974–1975) pp. C–101 & C–305.

*Primary Examiner*—Werren B. Lone
*Attorney, Agent, or Firm*—Sprung, Horn, Kramer & Woods

[57] ABSTRACT

A process for the preparation of 2-methylene aldehydes is disclosed wherein formaldehyde is reacted with an aldehyde of the general formula R—CH$_2$CHO, where R stands for a substituted or unsubstituted organic radical having from 2 to 12 carbon atoms. The reaction takes place in the presence of a mixture of a secondary amine and an organic carboxylic acid having up to 5 carbon atoms.

15 Claims, No Drawings

PROCESS FOR THE PREPARATION OF 2-METHYLENE ALDEHYDES

CROSS REFERENCE OF THE RELATED APPLICATION

This application is a continuation-in-part of copending application Ser. No. 106,211, filed Dec. 21, 1979.

BACKGROUND OF THE INVENTION

1. Field of the Invention

The invention relates to a process for the preparation of 2-methylene aldehydes by reacting aldehydes having at least two carbon atoms on the α-carbon atom with formaldehyde in the presence of a catalyst system consisting of a mixture of a secondary amine and an organic carboxylic acid.

2. Discussion of Prior Art

2-Methylene aldehydes (α-methylene aldehydes, α-alkylacroleins) can be prepared in a number of ways. For example, the reaction of ammonia or a primary or secondary amine, usually present as a salt such as hydrochloride, with formaldehyde and a compound containing a reactive hydrogen atom, generally known as the Mannich reaction, will yield the desired methylene compounds.

In accordance with the process described in U.S. Pat. No. 2,518,416, a mixture of an aldehyde which has a $CH_2$ group in the α position relative to the carbonyl group and of formaldehyde is passed through the melt of a salt formed of a primary or secondary amine and a strong acid.

In accordance with the process described in U.S. Pat. No. 2,639,295, the condensation of aliphatic aldehydes with formaldehyde is carried out in the presence of a piperidine hydrochloride, morpholine hydrochloride or an ammonium salt such as ammonium chloride.

One characteristic which the processes cited above have in common is that condensation takes place in the presence of salts of the amines or of the ammonia, which must be used in a stoichiometric amount or even in excess.

While in German patent No. 16 18 528 it is pointed out that α-methylene aldehydes can be obtained by reaction of aldehydes of the general formula $RCH_2$—CHO with formaldehyde in the presence of catalytic amounts of a primary or secondary amine, it is apparent that in all examples illustrating the process claimed the amine is always used in the form of its salt, and always in amounts greater than what might be regarded as catalytic amounts.

The requirement that the condensation of aldehydes which contain a $CH_2$ group in the α position relative to the carbonyl group with formaldehyde be carried out in the presence of large amounts of an amine militates against economic utilization of the reaction. Moreover, working with amine salts such as hydrochloride calls for the use of equipment made of high-alloy special steels or of enameled reactors if damage to the reactors due to stress-corrosion cracking, for example, is to be avoided.

Finally, in these prior-art processes conversion, selectivity and yield are unsatisfactory, which imposes a limit on their practical use.

Thus, there has been a need for a process for the preparation of 2-methylene aldehydes which does not have the drawbacks outlined and in which the starting materials are converted to the desired products through a readily performed reaction in high yield.

In accordance with U.S. patent application Ser. No. 106,211, assigned to the assignee hereof, the disclosure of which is hereby specifically incorporated herein by reference, catalysts of the same composition are used solely for the preparation of methacrolein. But while it was originally through that said process would lend itself only to the preparation of methacrolein, it has now surprisingly been found that the process in accordance with the invention can be used for the preparation of 2-methylene aldehydes generally by reaction of aldehydes of the formula R—$CH_2$—CHO with formaldehyde if the catalyst consists essentially of 0.01 to 0.05 mols of a secondary amine and 0.005 to 0.02 mol of the carboxylic acid, both molar amounts based on the aldehyde of the formula R—$CH_2$—CHO.

SUMMARY OF THE INVENTION

The invention relates to a process for the preparation of 2-methylene aldehydes by the catalytic reaction of aldehydes of the general formula R—$CH_2$—CHO, where R stands for substituted or unsubstituted organic radicals, especially alkyl, alkenyl and their cyclic counterparts, having from 2 to 12 carbon atoms, and formaldehyde. Said process is characterized in that a mixture of a secondary amine and an organic acid having up to 5 carbon atoms is used as catalyst system.

Organic acids suitable for use are formic acid, acetic acid and especially propionic acid, n-butyric acid, i-butyric acid, n-valeric acid and i-valeric acid. Mixtures of organic acids having up to 5 carbon atoms may also be used. From 0.005 to 0.02 mol of acid is used per mol of aldehyde.

The secondary amine constituting the second component of the catalyst system is used in an amount ranging from 0.01 to 0.05 mol per mol of aldehyde. Suitable secondary amines are dipropylamine, methylbutylamine and ethylbutylamine, for example. Particularly well suited is di-n-butylamine. However, higher secondary amines such as di-n-octylamine are also suited for use. Generally, there is employed more amine than carboxylic acid on a molar basis.

In contrast to the Mannich reaction, the new process entails a catalytic reaction since both the amine and the carboxylic acid are used, not in molar ratios but merely in catalytic amounts.

The formaldehyde and the aldehyde of the general formula R—$CH_2$—CHO may be used in a stoichiometric ratio. However, the formaldehyde may also be present in excess, up to 1.5 moles of formaldehyde being used per mol of aldehyde.

The formaldehyde is used either as an aqueous solution or as a polymer such as paraformaldehyde.

Particularly contemplated aldehydes of the formula R—$CH_2$—CHO include n-butyraldehyde, 3-methylbutanal n-valeraldehyde, n-hexanal, n-heptanal, n-octanal, n-nonanal, n-decanal, phenylacetaldehyde, cyclohexylacetaldehyde, β-phenylpropanal, β-formylpropionic acid methyl ester and β-formylpropionitrile.

The use of a solvent is not required but is advantageous when a polymeric form of formaldehyde is used. Suitable solvents are aliphatic alcohols and hydrocarbons as well as aromatic hydrocarbons such as 2-ethylhexanol, isododecane and toluene. The process does not require the use of chlorine.

The reaction is usually carried out as a liquid phase reaction, a reaction pressure ranging from 2 to 10, and preferably from 2 to 4, bars being maintained. However, the reaction may also be carried out in the gaseous phase. The reaction temperature ranges from 70° to 120° C., and preferably from 95° to 110° C.

When the reaction is carried out as a liquid-phase reaction, a pressure vessel is employed into which formaldehyde, aldehyde of the general formula R—CH$_2$—CHO and the carboxylic acid are first introduced under a nitrogen atmosphere, the secondary amine then being added proportionately, and advantageously with cooling and vigorous agitation. The reaction mixture is then heated to the reaction temperature and the reactants are allowed to react with one another. The reaction is completed after about 30 to 120 minutes. After cooling, the reaction mixture separates into an organic phase and an aqueous phase. The 2-methylene aldehydes are obtained from the crude product by fractional distillation in a yield of better than 90% based on the aldehyde used, and in a purity of better than 98%. For most end uses, further purification is not required.

The process in accordance with the invention permits the preparation of 2-methylene aldehydes at low temperatures and under conditions which do not require special apparatus. The reaction is readily performed; yet the yield of pure 2-methylene aldehydes is remarkably high.

The examples which follow will serve to illustrate the process in accordance with the invention.

TESTS CONDUCTED

1. Comparative Example

In a pressure vessel of 0.6 m$^3$ capacity equipped with an agitator, 1.75 kilomols of the aldehyde selected and 1.75 kilomols formaldehyde (in the form of a 30% aqueous solution) were mixed under a nitrogen atmosphere, and over a period of 30 minutes the amount of secondary amine specified in the Table was added to the mixture. Cooling was effected during the addition of the amine, which produced a temperature rise to about 30° C. in the pressure vessel. The reaction mixture was then heated to 95° to 100° C. over a period of 30 minutes. The pressure then ranged from 2 to 2.5 bars. The reaction was completed after about 60 minutes. The reaction mixture was cooled and the aqueous phase was separated. The gas-chromatographic analysis of the organic phase did not extend to such residual amounts of formaldehyde and water as may have been present.

2. Example

In a pressure vessel of 0.6 m$^3$ capacity equipped with an agitator, 1.75 kilomols of the aldehyde selected and 1.75 kilomols formaldehyde (in the form of a 30% aqueous solution) and the amount of the corresponding carboxylic acid specified in the Table were mixed under a nitrogen atmosphere. The further procedure (addition of amine; temperature, pressure; product separation) was the same as in the comparative example.

| PREPARATION OF ETHYL ACROLEIN | Comparative Example | Example 1 | Example 2 | Example 3 |
|---|---|---|---|---|
| Starting materials (kg) | | | | |
| n-Butyraldehyde | 126 | 126 | 126 | 126 |
| Formalin (30% sol.) | 175 | 175 | 175 | 175 |
| Di-n-butylamine | 5.75 | 5.75 | 5.75 | — |
| Di-n-octylamine | — | — | — | 12.5 |
| Propionic acid | — | 1.25 | — | 1.25 |
| n-Butyric acid | — | — | 1.25 | — |
| Gas-chromatic analysis (weight percent) | | | | |
| Leading Portion | Trace | Trace | Trace | 0.8 |
| Ethylacrolein | 69.0 | 92.0 | 91.6 | 87.2 |
| Component | 3.5 | 3.6 | 3.9 | 4.8 |
| Component | 3.9 | — | — | — |
| Trailing Portion | 23.6 | 4.4 | 4.5 | 7.2 |

| PREPARATION OF ISOPROPYLACROLEIN | Comparative Example | Example 4 | Example 5 | Example 6 | Example 7 |
|---|---|---|---|---|---|
| Starting materials (kg) | | | | | |
| 3-Methylbutanal | 150 | 150 | 150 | 150 | 150 |
| Formalin (30% sol.) | 175 | 175 | 175 | 175 | 175 |
| Di-n-butylamine | 6 | 6 | 6 | 6 | 6 |
| Isobutyric acid | — | 1.4 | — | — | — |
| 3-Methylbutyric acid | — | — | 1.65 | — | — |
| n-Valeric acid | — | — | — | 1.65 | — |
| n-Valeric acid 65% / 3-Methylbutyric acid 35% | — | — | — | — | 1.65 |
| Gas-chromatic analysis (weight percent) | | | | | |
| Leading portion | 2.2 | 1.6 | 1.7 | 1.7 | 1.6 |
| 3-Methylbutanal | 3.5 | 0.3 | 0.5 | 0.6 | 0.6 |
| Component | 1.5 | 0.1 | 0.1 | 0.1 | 0.1 |
| Isopropylacrolein | 64.6 | 92.4 | 92.0 | 91.7 | 91.8 |
| Component | 1.1 | 0.6 | 0.7 | 0.7 | 0.8 |
| Trailing portion | 27.1 | 5.0 | 5.0 | 5.2 | 5.1 |

In addition to the aforementioned organic carboxylic acids for use in the reaction, there can be employed oxylic acid, maleic acid, acetylene carboxylic acid, malonic acid, glutaric acid, succinic acid, tartaric acid, adipic acid, hydroxy succinic acid, salicyclic acid and 2-ethylhexanoic acid. Mixtures of these acids alone or with any one of the aforementioned acids or mixtures of the aforementioned acids can also be employed.

In addition to the secondary amines named specifically above, there can be employed other secondary amines, especially $C_1$–$C_8$ secondary amines including particularly secondary amines where the organic substituent is an alkyl group or where the nitrogen atom is a part of a heterocyclic ring. Suitable secondary amines in addition to those mentioned above include di-2- ethyhexyl amine, diphenyl amine, dicyclohexyl amine, diisooctyl amine, piperdine, pyrrolidine, piperazine, and morpholine.

What is claimed is:

1. A process for the preparation of a 2-methylene aldehyde which comprises contacting formaldehyde and an aldehyde of the formula R—CH$_2$—CHO, wherein R represents a substituted or unsubstituted organic radical having 2 to 12 carbon atoms in the presence of a secondary amine and an organic carboxylic acid having up to 5 carbon atoms, said secondary amine and said organic carboxylic acid being present in a catalytic amount.

2. A process according to claim 1, wherein said secondary amine is present in an amount of 0.01 to 0.05 mol and said carboxylic acid is present in an amount of 0.005 to 0.02 mols, both molar amounts being based upon the amount of aldehyde of the formula R—CH$_2$—CHO.

3. A process according to claim 2, wherein said secondary amine is present in excess with respect to the carboxylic acid.

4. A process according to claim 1, wherein the reaction is carried out at 70° to 120° C.

5. A process according to claim 4, wherein the reaction is carried out at 95° to 110° C.

6. A process according to claim 4, wherein the process is carried out at a pressure of 2 to 10 bars.

7. A process according to claim 6, wherein the process is carried out at a pressure of 2 to 4 bars.

8. A process according to claim 2, wherein the organic acid is selected from the group consisting of formic acid, acetic acid, propionic acid, n-butyric acid, i-butyric acid, n-valeric acid and i-valeric acid.

9. A process according to claim 2, wherein the secondary amine is selected from the group consisting of dipropylamine, methylbutylamine, and ethylbutylamine.

10. A process according to claim 2, wherein the secondary amine is di-n-octylamine.

11. A process according to claim 2, wherein the secondary amine is di-n-butylamine.

12. A process according to claim 2, wherein n-butyraldehyde is reacted with formaldehyde.

13. A process according to claim 2, wherein 3-methylbutanal is reacted with formaldehyde.

14. A process according to claim 2 wherein said aldehyde of the formula R—CH$_2$—CHO is 3-methylbutanal.

15. A process according to claim 2 wherein said aldehyde of the formula R—CH$_2$—CHO is n-butyraldehyde.

* * * * *